United States Patent [19]

Leavesley

[11] Patent Number: 5,601,708
[45] Date of Patent: Feb. 11, 1997

[54] APPARATUS FOR PRESSURIZING A REMOVABLE CHROMATOGRAPHY CARTRIDGE

[75] Inventor: Peter J. Leavesley, Charlottesville, Va.

[73] Assignee: Dyax Corp., Cambridge, Mass.

[21] Appl. No.: 528,060

[22] Filed: Sep. 14, 1995

Related U.S. Application Data

[63] Continuation of Ser. No. 224,264, Apr. 7, 1994, abandoned.

[51] Int. Cl.$^6$ .................................................. B01D 15/08
[52] U.S. Cl. ........................ 210/198.2; 210/656; 96/101
[58] Field of Search ................................ 210/635, 656, 210/659, 198.2, 232, 238, 282; 96/101, 106

[56] References Cited

U.S. PATENT DOCUMENTS

| | | | |
|---|---|---|---|
| 2,966,990 | 1/1961 | Sicard | 210/282 |
| 3,050,191 | 8/1962 | Gillick | 210/282 |
| 3,254,771 | 6/1966 | Sicard | 210/282 |
| 3,262,570 | 7/1966 | Gailitis | 210/282 |
| 3,321,085 | 5/1967 | Moorhead | 210/282 |
| 3,415,382 | 12/1968 | Martin | 210/282 |
| 3,469,696 | 9/1969 | Petrucci | 210/282 |
| 3,483,986 | 12/1969 | Wright | 210/282 |
| 3,682,315 | 8/1972 | Haller | 210/282 |
| 3,950,251 | 4/1976 | Hiller | 210/282 |
| 4,093,550 | 6/1978 | Stahl | 210/198.2 |
| 4,250,035 | 2/1981 | McDonald | 210/198.2 |
| 4,283,280 | 8/1981 | Brownlee | 210/198.2 |
| 4,384,957 | 5/1983 | Crowder | 210/198.2 |
| 4,565,632 | 1/1986 | Hatch | 210/198.2 |
| 4,587,014 | 5/1986 | America | 210/198.2 |
| 4,719,011 | 1/1988 | Shalon | 210/198.2 |
| 4,737,284 | 4/1988 | Hauke | 210/198.2 |
| 4,737,292 | 4/1988 | Ritacco et al. | 210/198.2 |
| 4,806,238 | 2/1989 | Sattler | 210/198.2 |
| 4,874,520 | 10/1989 | Lee | 210/198.2 |
| 4,876,005 | 10/1989 | America | 210/198.2 |
| 4,968,421 | 11/1990 | Spacek | 210/198.2 |
| 4,986,909 | 1/1991 | Rai | 210/198.2 |
| 4,994,180 | 2/1991 | Sims | 210/198.2 |
| 5,167,809 | 12/1992 | Mann | 210/198.2 |
| 5,227,059 | 7/1993 | Shepherd | 210/198.2 |
| 5,238,556 | 8/1993 | Shirkhan | 210/198.2 |
| 5,265,642 | 11/1993 | Buckminster | 210/198.2 |
| 5,324,427 | 6/1994 | Traveset-Masanes | 210/198.2 |

OTHER PUBLICATIONS

Cuno Catalog 1992, pp. 1–5, 7, 8, 34, 41 and 47.
Biotase Product Brief Kiloprep® 100 Compression Module Jun. 1993, two pages.
Kiloprep® 100 Compression Module User Manual, Dec. 17, 1992, pp. 1–26.

*Primary Examiner*—Ernest G. Therkorn
*Attorney, Agent, or Firm*—Fish & Richardson P.C.

[57] ABSTRACT

Chromatography apparatus including an enclosure having a pressurizable chamber sized to removably receive a chromatography cartridge therein and an opening to the chamber, and a cap that closes the opening and has a flow passage for directing a sample to be analyzed to the cartridge, the cap having a sharp protruding member that surrounds the flow opening and makes sealable engagement with the cartridge by digging into the cartridge.

16 Claims, 1 Drawing Sheet

:::page-number
5,601,708
:::

APPARATUS FOR PRESSURIZING A REMOVABLE CHROMATOGRAPHY CARTRIDGE

This is a continuation of application Ser. No. 08/224,264, filed Apr. 7, 1994, now abandoned.

BACKGROUND OF THE INVENTION

The invention relates to apparatus used to pressurize a removable chromatography cartridge.

In chromatographic procedures, a stationary phase such as a surface active powder is contained in a chromatography column. A mobile phase consisting of a carrier fluid and a sample of chemical to be identified, analyzed, or purified is passed through the column. Different components of the sample pass through the column at different rates and are thereby separated from each other, leaving the column at different times.

Voids in the stationary phase that may have resulted during shipping and other nonuniform packing conditions can deleteriously affect the operation of a chromatography column and the accuracy of the results. It is known to compress flexible-walled columns in order to close voids and provide uniform packing of the stationary phase. E.g., in U.S. Pat. No. 4,250,035, a chromatography column is made of polytetrafluoroethylene (PTFE) tubing sealed at the ends with porous frits. In one embodiment, the column is placed within a chamber that is pressurized to compress the deformable walls of the column and the stationary phase therein. This provides a uniform packing of the stationary phase and promotes the accuracy of the chromatography column.

It is also known to make a chromatography cartridge from polyethylene, or like material, and to mount the cartridge in a pressurizable compression module assembly having an outer cylindrical body and an end cap that has an O-ring around its outer surface for providing a seal with the end of the cartridge. The O-ring is made of resilient, flexible material, so as to provide a good seal, and is chemically-resistant, to reduce interaction with the mobile phase chemicals. Nevertheless, this O-ring may shrink or swell, leach compounds into the column or absorb the sample.

SUMMARY OF THE INVENTION

The invention features, in general, chromatography apparatus that includes an enclosure having a pressurizable chamber for receiving a chromatography cartridge therein and a cap for closing an opening to the enclosure. The cap has a sealing structure for mating with the enclosure and providing a seal to the enclosure around the opening. The cap also has a flow passage for directing a sample to be analyzed to the cartridge therein. The cap also has a sharp protruding member that surrounds the flow passage, is inside of the cap sealing structure, and is directed toward the chamber for making sealable engagement with the cartridge by digging into the cartridge. The sharp protruding member provides a reliable, long-lasting sealing structure that can be repeatedly used to make seals with removable chromatography cartridges without employing an O-ring, which can wear in use and will need to be replaced at significant expense.

In preferred embodiments, the apparatus has a mechanism to force the sharp protruding member into the wall of the cartridge. This mechanism can be provided by camming surfaces on the enclosure and the cap and a V-band that engages both camming surfaces and brings the enclosure and cap together as the band is tightened. The chromatography cartridge has a porous frit in a recess therein, and the cap has a plug portion sized to contact the frit. The sharp protruding member is preferably angular in section with two converging lines meeting at a point, the lines making an angle of between 20° and 120° (most preferably, between 50° and 90°). The protruding member preferably extends between 0.03" and 0.15" (most preferably between 0.05" and 0.10"). The enclosure preferably is cylindrical and has a pressure inlet for connecting to a source of pressurized liquid and a pressure relief valve.

Other advantages and features of the invention will be apparent from the description of the preferred embodiment thereof and from the claims.

DESCRIPTION OF THE PREFERRED EMBODIMENT

Figure 1:
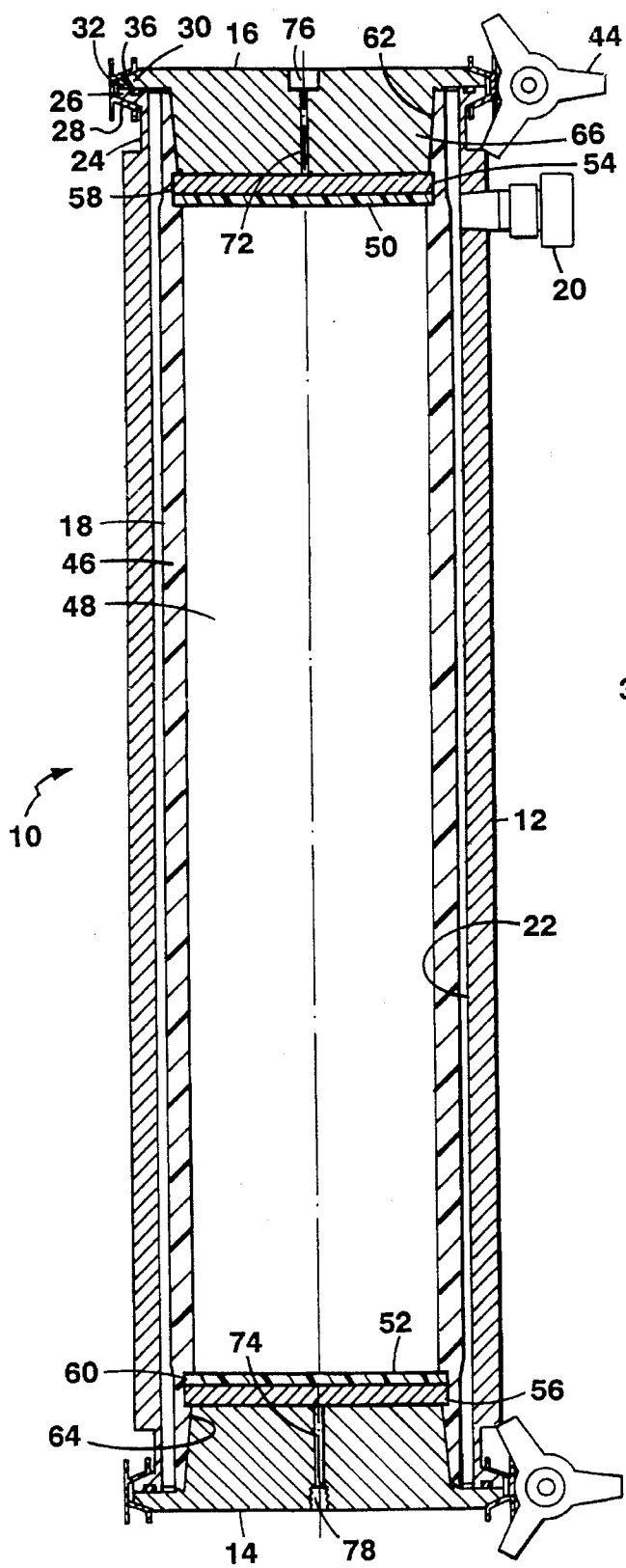
FIG. 1 is a sectional view of chromatography apparatus according to the invention.
Figure 2:
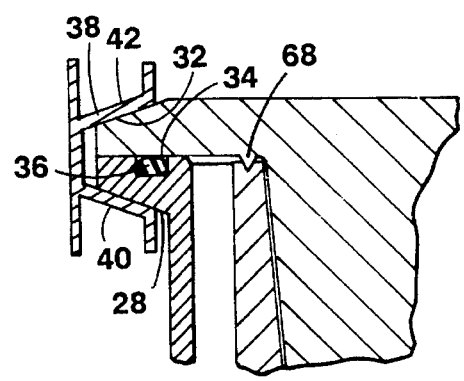
FIG. 2 is an enlarged view of a portion of FIG. 1 showing the sealing engagement between an end cap and an enclosure and between the end cap and a removable chromatography cartridge of the FIG. 1 apparatus.

Referring to the figures, chromatography apparatus 10 includes outer barrel 12, end caps 14, 16, and removable chromatography cartridge 18 within barrel 12 and between end caps 14, 16. Barrel 12 has pressure relief valve 20 in an opening to inner chamber 22. Barrel 12 acts as an enclosure for receiving and pressurizing cartridge 18 therein.

At both ends of barrel 12 are outer, annular recesses 24 and flanged ends 26 having inclined camming surfaces 28. End caps 14, 16 have mating flanges 30 with oppositely inclined camming surfaces 32. Flanged ends 26 also have an axially-directed annular recesses 34 containing sealing rings 36 therein. V-band 38 has inclined surfaces 40, 42 engaging camming surfaces 28, 32, respectively. V-band clamping knob 44 increases the tension in V-band 38, and, in so doing, biases end cap 16 axially toward barrel 12.

Chromatography cartridge 18 includes cylinder 46 made of food-grade, medium-density polyethylene and has a nominal inner diameter of three inches. Stationary phase media 48 is contained within cylinder 46 between thin porous frits 50, 52 and thick frits 54, 56, respectively. Frits 50 and 54 are received within inwardly directed annular recess 58, and frits 52 and 56 are received within inwardly directed annular recess 60. Cylinder 46 extends beyond frits 54, 56 and has diverging, inner conical surfaces 62, 64. End caps 14, 16 each have plug portions 66 with outer conical surfaces that mate with surfaces 62, 64 of cartridge 18.

Figure 3:
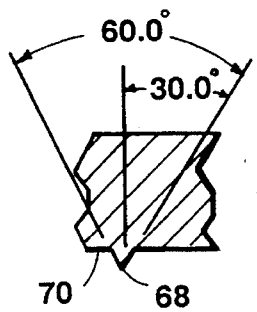
FIG. 3 is a sectional view of a portion of the FIG. 1 end cap providing a knife edge sealing member.

Just outside of plug 66, each flange 30 has sharp protruding member 68 having a radius equal to the radius at the midsection at the end of the wall of cylinder 46. End caps 14, 16 are made of metal, and the ends of protruding member 68 are sharp so that they dig into the ends of the polyethylene cylinder 46 when force is applied to bring caps 14, 16 toward barrel 12 by V-bands 38. Referring to FIG. 3, it is seen that protruding member 68 makes a 60° angle in section and protrudes downward from surface 70 by 0.060"–0.065". Other angles (e.g., 20° to 120°, preferably 50° to 90°) and distances (e.g. 0.03" to 0.15", preferably 0.05" to 0.10")

could work. End caps 14, 16 also have flow passages 72, 74 through them. Passage 72 communicates with process inlet 76, and flow passage 74 communicates with process outlet 78.

In use, chromatography cartridge 18 can be installed in barrel 12 and easily removed and replaced with another cartridge when it is necessary to change to a different or new chromatographic media. A variety of stationary phase media may be used in the cartridges. The most commonly used are reverse phase, normal phase, ion-exchange, and size-exclusion packings.

When a new cartridge 18 is installed, it is inserted into barrel 12, and end caps 14 and 16 are moved into position. V-bands 38 are placed around flanged ends 28 and flanges 30 and are tightened with V-band clamping knobs 44. As V-bands 38 are tightened, flanged ends 28 and flanges 30 come closer together, compressing O-rings 36, and causing protruding members 68 to dig into the ends of cylinder 46. Because protruding members 68 are made of metal, they dig into the softer polyethylene cylinder 46. Protruding member 68 and side surface 70 is spaced with respect to the bottom of plug portions 66 so that the inner surfaces of plug portions 66 contact thick frits 54, 56 when flanged ends 28 and flanges 30 have been brought together. Protruding sealing member 68 provides a good seal between end caps 14, 16 and cylinder 46 without the need for O-rings with chemically resistant properties at these locations.

After cartridge 18 has been installed, chamber 22 is pressurized, via an opening not shown on the drawings, and the increased pressure compresses the walls of flexible polyethylene cylinder 46, providing uniform packing for the stationary phase media therein. A source of sample in a carrier liquid is connected to process inlet 76, and liquid leaves enclosure 12 via process outlet 78.

Other embodiments of the invention are within the scope of the appended claims. E.g., in place of V-band 38, other mechanisms could be used to hold end caps 14, 16 in place and bring them together. Also, other geometries could be used for protruding member 68.

What is claimed is:

1. Chromatography apparatus comprising
a replaceable chromatography cartridge having a thin, flexible outer wall that has a processing chamber therein that contains a stationary phase, said wall being deformable in response to a pressure differential across said outer wall to compress said stationary phase therein, said cartridge having an inlet end defining an inlet to said cartridge and an outlet end defining an outlet of said cartridge, said outer wall having an inlet peripheral end surface around said inlet in a plane transverse to an axis from said inlet to said outlet, said outer wall having an outlet peripheral end surface around said outlet in a plane transverse to said axis,
an enclosure having a pressurizable chamber sized to removably receive said chromatography cartridge therein and apply pressure to the outside of said cartridge so as to affect conditions within said processing chamber within said cartridge,
said enclosure having an opening to said pressurizable chamber sized to receive said chromatography cartridge therethrough,
said enclosure having an enclosure sealing structure surrounding said opening, and
a cap sized to close said opening and having a flow passage for directing a sample to be analyzed to said processing chamber within said cartridge when said cartridge is in said pressurizable chamber,
said cap having a cap sealing structure for mating with said enclosure sealing structure to make a sealable connection therewith around said opening,
said cap having a sharp protruding member that surrounds said flow passage, is inside of said cap sealing structure, and is directed toward said pressurizable chamber for making sealable engagement with said cartridge therein by digging into said inlet peripheral end surface of said wall of said cartridge, whereby said sharp protruding member provides a sealable connection for said flow passage through said cap to said processing chamber within said cartridge and separates said processing chamber from said pressurizable chamber.

2. The apparatus of claim 1 further wherein said enclosure has a second opening to said chamber and a second enclosure sealing structure surrounding said opening, and further comprising a second cap sized to close said second opening and having a second flow passage for liquid from said cartridge, said second cap having a second cap-sealing structure and a second sharp protruding member that surrounds second flow passage and makes sealable engagement with said cartridge.

3. The apparatus of claim 1 wherein said wall of said cartridge is made of plastic.

4. The apparatus of claim 3 further comprising means to force said sharp protruding members against said cartridge.

5. The apparatus of claim 4 wherein said enclosure is cylindrical, said cartridge is cylindrical, and said sharp protruding member is annular.

6. The apparatus of claim 3 wherein said cartridge has porous frits in respective recesses in said wall of said cartridge.

7. The apparatus of claim 6 wherein said end caps have flanges on which said sharp protruding members are located and plug portions located with respect to said flanges so as to contact said porous frit.

8. The apparatus of claim 1 further comprising means to force said sharp protruding member against said cartridge.

9. The apparatus of claim 8 wherein said cap and said enclosure have camming surfaces, and wherein said means to force is a V-band having camming surfaces that interact with mating camming surfaces on said cap and said enclosure.

10. The apparatus of claim 1 wherein said cartridge has a porous frit covering an opening to said cartridge.

11. The apparatus of claim 1 wherein said sharp protruding member has surfaces that, in section, form an angle of between 20° and 120°.

12. The apparatus of claim 1 wherein said sharp protruding member has surfaces that, in section, form an angle of between 50° and 90°.

13. The apparatus of claim 12 wherein said enclosure has a pressure relief valve.

14. The apparatus of claim 1 wherein said sharp protruding member has a height of between 0.03" and 0.15".

15. The apparatus of claim 1 wherein said sharp protruding member has a height of between 0.05" and 0.10".

16. The apparatus of claim 1 wherein said sharp protruding member is made of metal.

* * * * *